United States Patent [19]

Termine et al.

[11] Patent Number: 5,346,938
[45] Date of Patent: Sep. 13, 1994

[54] SMOKE SUPPRESSED FLAME RETARDANT UNSATURATED POLYESTER RESIN COMPOSITIONS

[75] Inventors: Enrico J. Termine; Nicolai A. Favstritsky, both of Lafayette; Kevin G. Taylor, W. Lafayette, all of Ind.

[73] Assignee: Great Lakes Chemical Corp., W. Lafayette, Ind.

[21] Appl. No.: 725,341

[22] Filed: Jul. 3, 1991

Related U.S. Application Data

[63] Continuation-in-part of Ser. No. 408,143, Sep. 15, 1989, abandoned, which is a continuation-in-part of Ser. No. 289,973, Dec. 22, 1988, abandoned.

[51] Int. Cl.$^5$ ............................ C08K 3/22; C08K 3/40; C08K 5/521
[52] U.S. Cl. ............................... 524/117; 524/436; 524/437; 524/494
[58] Field of Search ................. 524/117, 436, 437, 494

[56] References Cited

U.S. PATENT DOCUMENTS

| | | | |
|---|---|---|---|
| 3,293,327 | 12/1966 | Hechenbleikner et al. | 260/117 |
| 3,873,496 | 3/1975 | Hills et al. | 524/119 |
| 4,341,694 | 7/1982 | Halpern et al. | 524/119 |
| 4,724,107 | 2/1988 | McConnell et al. | 524/371 |
| 4,801,625 | 1/1989 | Parr et al. | 524/117 |

FOREIGN PATENT DOCUMENTS 0999793  7/1965  United Kingdom .

OTHER PUBLICATIONS

Taschenbuch der Kunststoff–Additive, Stabilisatoren, Hilfsstoffe, Weichmacher, Füllstoffe, Verstärkungsmittel, Farbmittel, 2. Ausgabe, Herausgegeben von Dr. R. Gächter und Dr. H. Müller, 2d Edition, Publisher Carl Hanser Verlag, Munich, Vienna, pp. 564–567 (1983).
*Modern Plastics Encyclopedia* vol. 63, No. 10A, McGraw Hill, Inc. pp. 179–180 (1986).

*Primary Examiner*—Kriellion S. Morgan
*Attorney, Agent, or Firm*—Woodard, Emhardt, Naughton, Moriarty & McNett

[57] ABSTRACT

Smoke suppressed flame retardant thermoset resin compositions comprise smoke suppressant bicyclic phosphate compound(s), flame retardant(s) and unsaturated polyester or other thermoset materials. These compositions exhibit a reduced tendency to smoke under conditions of burning.

12 Claims, No Drawings

SMOKE SUPPRESSED FLAME RETARDANT UNSATURATED POLYESTER RESIN COMPOSITIONS

REFERENCE TO RELATED APPLICATIONS

This application is a continuation-in-part of co-pending application Ser. No. 07/408,143, filed Sep. 15, 1989, now abandoned, which is a continuation-in-part of co-pending application Ser. No. 07/289,973, filed Dec. 22, 1988 now abandoned.

BACKGROUND OF THE INVENTION

1. Field of the Invention

This invention relates to thermoset polymers and specifically to additives which provide smoke suppression to unsaturated polyester ("UPE") and other thermoset resin compositions and enhance the effect of flame retardant agents incorporated therewith.

2. Description of the Prior Art

It is known in the art that the flammability of thermoset resins such as unsaturated polyesters can be reduced by incorporation of a flame retardant agent. Typical flame retardant agents include reactive or additive halogenated organic compounds, inorganic fillers, and special formulations based on phosphorous and ammonium salts.

Although efficient in suppressing the rate of combustion in a resin system, most flame retardants tend to affect adversely one or more key properties of the resin. For example, many flame retardant additives are ineffective at producing low smoke ("smoke suppressed") formulations.

Recent public awareness about risk and hazard assessment during fire situations, and technical limitations of conventional flame retardant additives warrant a need for improved flame retardant thermoset compositions. In particular, a need exists for a thermoset composition that passes flammability standards with low smoke and combustion by-product formation, and does not detract from overall polymer performance.

Many prior art references describe the use of a variety of smoke additives in unsaturated polyesters. *Modern Plastics Encyclopedia,* Vol. 63, No. 10A, McGraw-Hill, Inc., pp. 179–180 (1986). However, the selection of a suitable smoke suppressant for thermoset resins is not predictable. Selection is particularly difficult when flame retardants are employed, exacerbated by the complex interaction between the polymer and the flame retardant agent.

Hechenbleikner, et al. describe in U.S. Pat. No. 3,293,327 the production of bicyclic phosphites, phosphonates, thiophosphates, and selenophosphates. These compositions are said to be stabilizers for vinyl halide resins. They are alleged to be useful as heat stabilizers for vinyl chloride resin, and as antioxidants for fats and oils. The Hechenbleikner patent does not specify the use of bicyclic phosphates to achieve low smoke thermoset resin compositions, nor does it disclose that cyclic phosphates of the present invention could be used with flame retardant agents to produce smoke suppressed flame retardant thermoset compositions.

British Patent No. 999,793 describes a process for producing organic phosphates by subjecting organic phosphites to reaction with peracetic acid. This patent shows a method for producing the most preferred bicyclic phosphate of the present invention, 2,6,7-trioxa-1-phosphobicyclo[2.2.2]-octane-4-methanol -1-oxide and teaches the use of acetal ring-containing phosphates as plasticizers or functional fluids. The British patent, however, does not disclose the present invention. It does not mention bicyclic phosphates as being useful for flame retardant thermoset resins, nor that the most preferred bicyclic phosphate of the present invention can be used with flame retardant additives to yield improved thermoset compositions.

Hills, et al. describe in U.S. Pat. No. 3,873,496 a flame retardant polyester composition which contains 5 to 25 percent of a hydroxymethyl bicyclic phosphate compound as a flame retardant additive. Hills did not observe the ability for bicyclic phosphates to act as smoke suppressors for thermoset resin compositions which employ other compounds as the primary flame retardant additive.

Halpern, et al. describe in U.S. Pat. No. 4,341,694 a composition comprising 2,6,7-trioxa-1-phosphobicyclo[2.2.2]-octane-4-methanol-1-oxide and a nitrogen-containing co-additive, which are intumescent and are adaptable to flame retard polyolefins, polyvinylaromatic resins, polycarbonates, PVC and blends thereof. Halpern did not observe any smoke suppression of the present invention. Further, the present invention is not directed to providing intumescence, and operates in the absence of nitrogen compounds required by Halpern, namely compounds which are effective with the phosphates to provide intumescence, comprising ammonium compounds and derivatives of ammonia including amines, ureas, guanidines, guanamines, s-triazines such as melamine and ammeline, amino acids and peptides, as well as salts and derivatives thereof.

Parr, et al. describe in U.S. Pat. No. 4,801,625 a flame resistant composition having (1) an organic polymeric substance in intimate contact with (2) a bicyclic phosphorous compound, and (3) a gas producing compound. Parr is silent on the use of bicyclic compounds to attain smoke suppressed flame retardant thermoset compositions.

Accordingly, a primary object of this invention is to provide smoke suppressed flame retardant thermoset resin compositions.

A related object is to provide flame retardant unsaturated polyester resin compositions with a reduced tendency to smoke under burning conditions. A further object is to provide unsaturated polyester resin compositions incorporating bicyclic phosphate compound and flame retardant agents.

SUMMARY OF THE INVENTION

The foregoing and other objects, advantages and features of the present invention may be achievable with smoke suppressed thermoset resin compositions incorporating an additive mixture comprising a flame retardant agent and a smoke suppressant bicyclic phosphate compound of the the following Formula (I):

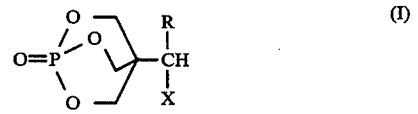

where X is OH, OR', or OC(O)R'; R is H or a saturated or unsaturated straight-chain or branched-chain $C_1$–$C_{17}$ alkyl; and R' is a saturated or unsaturated straight-chain or branched-chain $C_1$–$C_{17}$ alkyl. The present invention is particularly useful with isophthalic unsaturated polyesters, orthophthalic unsaturated polyesters, vinylester resins, and epoxy resins. Compositions in accordance with this invention exhibit a reduced tendency to smoke under burning conditions.

DESCRIPTION OF THE PREFERRED EMBODIMENTS

This invention relates to smoke suppressed flame retardant thermoset resin compositions. In particular, the invention relates to unsaturated polyesters, vinylester resins and epoxy resin compositions which are flame retardant and which exhibit a reduced tendency to smoke when burning. Compositions in accordance with this invention incorporate an additive mixture comprising one or more smoke suppressant bicyclic phosphate compounds and one or more halogen-containing flame retardants. It has been discovered that the indicated compositions, having flame retardant agents therewith, have a reduced tendency to smoke, and this result is achieved in the absence of nitrogen compounds including those utilized by Halpern in U.S. Pat. No. 4,341,694.

Preferred bicyclic phosphates in accordance with this invention are compounds of Formula (I) where X is OH or OC(O)R'. The most preferred bicyclic compounds are 2,6,7-trioxa- phosphobicyclo[2.2.2]-octane-4-methanol-1-oxide (Compound BCP, that is, Formula [I] when R is H and X is OH), and 2,6,7-trioxa-1-phosphobicyclo[2.2.2]-octane-4-methanol, acetate, 1-oxide (Compound BCP-A, that is, when R is H and X is OC-(O)CH$_3$).

The flame retardant agent employed in accordance with the present invention may be any common flame retardant agent which can be used to reduce the flammability of thermoset resins, such as halogenated compounds containing bromine and chlorine, or inorganic materials, such as metal hydrates, metal borates, antimony-containing compounds, or phosphorous-containing compounds.

Preferred halogen-containing compounds are di(octyl)tetrabromophthalate, hexabromocyclododecane, tetrabromobisphenol A, tetrabromobisphenol A bis-(dibromopropylether), dibromo(dibromoethyl)cyclohexane, tetrabromocyclooctane, bis-(dibromonorbornane dicarboximido)ethane, bis-(tetrabromophthalimido)ethane, Dieis-Alder adduct of chlorinated cyclopentadiene and unsaturated cycloaliphatic compound, bis-(tribromophenoxyethyl)- tetrabromobisphenol A ether, pentabromodiphenyl ether, octabromodiphenyl ether, decabromodiphenyl ether, bis-(tribromophenoxy)ethane, bis-(pentabromophenoxy)ethane, chloropentabromocyclohexane, (tribromophenoxy)- (dibromononylphenoxy)ethane, pentabromoethylbenzene, pentabromododecylbenzene, carbonate oligomers of tetrabromobisphenol A, poly(bromostyrene), and brominated polystyrene, poly(bromophenylene) ether, and mixtures thereof.

Substantially any suitable metal hydrates and oxides may be employed as flame retardant agents, including hydrates and oxides of aluminum, iron, zinc, magnesium, tin, molybdenum and antimony. Alumina trihydrate, magnesium hydroxide, and antimony trioxide are the preferred compounds in this class.

Suitable metal boron-containing flame retardant compounds include zinc, barium, calcium, magnesium, cadmium and mercury. Zinc borate is the preferred compound in this class.

Substantially any suitable phosphorus-containing compound may be used as a flame retardant agent, including ammonium polyphosphate, arylphosphates and alkarylphosphates. Particularly preferred are alkaryl phosphates commercially available from FMC Corporation under the trademarks Kronitex 100 and Santicizer 148.

The foregoing flame retardant compounds are added to thermoplastic resins at levels such that the resultant resin composition may be rendered flame retardant.

Thermoset resins which may be treated in accordance with the invention include thermosets such as polyesters, epoxies, vinylesters, alkyl polyesters, melamine isocyanurates, polyurethanes, phenolic resins and phenylene-based resins. Isophthalic and orthophthalic unsaturated polyesters, vinylester resins and epoxy resins are preferred thermosets in accordance with this invention.

It is customary to provide thermoset resins such as unsaturated polyesters with glass fiber reinforcements. Glass fiber reinforcements may usefully be employed at a level of about 5 to 60 percent by weight of the composition, preferably about 10 to 40 percent by weight.

The scope of the present invention also includes the incorporation of other additives in the composition so far as to produce a particular end result. Such additives include, without limitation, blowing agents, heat stabilizers, light stabilizers, plasticizers, pigments, preservatives, ultraviolet light stabilizers, fillers, antioxidants, antistatic agents and other materials well known to those skilled in the art, for example, as described in *Modern Plastics Encyclopedia*, Vol. 63, No. 10A, McGraw-Hill, Inc. (1986).

The bicyclic phosphates of the present invention may be used alone or as mixtures of any such compounds. When mixtures of bicyclic phosphates are employed, substantially any combinations of amounts and proportions of the individual compounds may be used. The use of Compound BCP and Compound BCP-A is especially preferred in accordance with this invention.

The bicyclic phosphate may be employed at substantially any level because even very low levels are believed to assist in smoke suppression. Desirably, bicyclic phosphates are present at a level of about 1 to 30 percent, preferably about 5 to 25 percent, and most preferably about 10 to 20 percent, all by weight of the composition.

The flame retardant agents of the present invention may be used alone or as mixtures of any such compounds. When mixtures of flame agents are employed, substantially any combinations of amounts and proportions of the individual compounds may be used. The use of di-(2-ethylhexyl)tetrabromophthalate, alumina trihydrate, magnesium hydroxide, zinc borate, antimony tioxide, and alkaryl phosphates are especially preferred in accordance with this invention. Preferably flame retardants are employed at a level of about 1 to 65 percent by weight of the composition, preferably about 5 to 45 percent, and most preferably about 30 to 40 percent, depending on the particular resin system and retardant employed. Desirably, the bicyclic phosphate compound and flame retardant are provided as a mixture useful as an additive which may be added to the thermoset resin compositions. The additive mixture utilizes bicyclic phosphate and flame retardant in a weight ratio lying in the range of about 1:25 to 20:1, most preferably, about 3:20 to 20:3.

The additive mixture is incorporated into the polymer composition at a level such that the resulting resin composition is rendered flame retardant. In general, the additive mixture is provided in the flame retardant at a level of about 2–50 percent by weight of the resin composition, preferably about 3–30 percent by weight.

Practice of the present invention is illustrated by the following examples, which are given to illustrate the invention and should not be construed as limiting its scope.

EXAMPLES

Preparation of Unsaturated Polyesters

Unsaturated polyesters ("UPE") thermosets were prepared by standard hand lay-up procedures. Koppers Dion 810 isophthalic unsaturated polyester resin was used in all cases. Uncured resin was promoted with cobalt naphthenate, blended with fillers, additives, and glass reinforcing agent. The mixture was degased in a vacuum oven, treated with methyl ethyl ketone ("MEK") peroxide catalyst, and cured at room temperature for 12 hours followed by 1 hour at 100/C. The general composition of the samples in parts by weight ("PBW") is given in the following chart.

| USPE Formulations | |
| --- | --- |
| Component | PBW |
| Koppers Dion 810 Isophthalic Resin | varied |
| Flame Retardant | varied |
| Chopped Strand Glass | 20 |
| TiO$_2$ | 1 |
| MEK Peroxide | 1 |
| Cobalt Naphthenate | 0.5 |

The specific composition of each sample prepared using this methodology is given in Table I, These samples were subjected to a series of standard test procedures as described below,

Flammability Test Procedures

The following test protocols were used for the samples prepared in the foregoing manner.

| Test Method | Description |
| --- | --- |
| Four Foot Tunnel Test | Apparatus to measure flame spread and smoke development in accordance with ASTM-E-84 test procedures. The length of the specimen was four feet instead of 25 feet. Lower values for flame spread and smoke development |
| HLT-1 Vertical Flame Test | indicate improved performance. A test method which ranks specimen based on time to extinguish a flame after ignition. The highest rating (best performance) is 100. |

Each of the test samples was subjected to these tests. The data are given in Table I.

TABLE I

| EXAMPLE NUMBER | BCP wt % | FLAME RETARDANT TYPE | AMOUNT wt % | FOUR FT. TUNNEL FLAME SPREAD | SMOKE DEVELOPMENT | HLT-15 ASTM | HARDNESS BARCOL ASTM |
| --- | --- | --- | --- | --- | --- | --- | --- |
| CONTROL | 15 | — | 0 | 19 | 140 | 92 | 62 |
| 1 | 15 | ATH | 38 | 16 | 80 | 100 | 45 |
| COMP 1 | 0 | ATH | 38 | 36 | 600 | 36 | 48 |
| 2 | 15 | MgOH | 38 | 17 | 85 | 100 | 45 |
| COMP 2 | 0 | MgOH | 38 | 39 | 640 | 24 | 47 |
| 3 | 15 | ZnBor | 38 | 19 | 120 | 96 | 44 |
| COMP 3 | 0 | ZnBor | 38 | 53 | 945 | 24 | 48 |

BCP - Preferred bicyclic phosphate
ATH - alumina trihydrate
MgOH - magnesium hydroxide
ZnBor - zinc borate These data demonstrate the patentability of the subject invention. The Control Example shows the effect of 15.0% BCP on flame spread and smoke development, as measured by the four foot tunnel testing for isophthalic polyester thermoset composites. Comparative Examples 1–3 show the effect of various flame retardants on flammability performance when Compound BCP is not present. Examples 1–3 illustrate the invention using the same flame retardant agents in combination with Compound BCP.

In every case, compositions comprising Compound BCP had lower smoke development than the Control Example (a system without additional flame retardant agents) or the corresponding Comparative Examples 1–3 (i.e., systems without Compound BCP).

Moreover, compositions containing BCP did not affect physical property performance, as exemplified by the minimal change in Hardness.

The data set forth in Table II shows a comparison of the use of BCP with melaminium hydrobromide in unsaturated polyester resin. The incorporation of the melaminium hydrobromide substantially increased the flame spread and smoke in the four foot tunnel testing.

TABLE II

Use of BCP with Melaminium Hydrobromide in Unsaturated Polyester Resin

| Formulation | 1 | 2 |
| --- | --- | --- |
| Polyester Resin | 48 | 44.4 |
| BCP | 23 | 23 |
| Melaminium Hydrobromide | 0 | 5 |
| Glass | 24.4 | 23 |
| TiO$_2$ | 2 | 2 |
| MEK Peroxide | 2.2 | 2.2 |
| Cobalt Napthenate | 0.4 | 0.4 |
| Properties | | |
| Four Foot Tunnel | | |
| Flame Spread | 13 | 19 |
| Smoke Development | 100 | 122 |

What is claimed is:

1. A smoke suppressed thermoset resin composition comprising:
   a thermoset polyester resin; and
   a mixture comprising:
   at least one flame retardant agent selected from alumina trihydrate or magnesium hydroxide; and
   a smoke suppressant comprising at least one bicyclic phosphate compound of the formula:

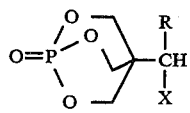

where X is OH, OR' or OC(O)R'; R is H or a saturated or unsaturated straight-chain or branched-chain $C_1$–$C_{17}$ alkyl; and R' is a saturated or unsaturated $C_1$–$C_{17}$ alkyl.

2. A composition, as claimed in claim 1, wherein the bicyclic phosphate compound is 2,6,7-trioxa-phosphobicyclo [2.2.2]-octane-4-methanol-1-oxide; or 2,6,7-trioxa-1-phosphobicyclo[2.2.2]-octane-4-methanol, acetate, 1-oxide.

3. A composition as claimed in claim 1, wherein the resin is an unsaturated polyester.

4. A composition as claimed in claim 1, wherein the weight ratio of bicyclic phosphate compound to flame retardant agent lies in the range of about 1:25 to 20:1.

5. A composition, as claimed in claim 1, wherein the mixture of bicyclic phosphate compound and flame retardant agent is provided in the resin composition at a level lying in the range of about 2–50 percent by weight of the overall composition.

6. A composition, as claimed in claim 5, wherein the composition additionally comprises glass fiber reinforcements.

7. A method for suppressing the tendency of thermoset polyester resin compositions to smoke under conditions of burning comprising the step of incorporating therein an effective amount of a mixture comprising:
   a flame retardant agent selected from alumina trihydrate or magnesium hydroxide; and
   a smoke suppressant comprising at least one bicyclic phosphate compound of the formula:

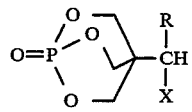

where X is OH, OR' or OC(O)R'; R is H or a saturated or unsaturated straight-chain or branched-chain $C_1$–$C_{17}$ alkyl.

8. A method, as claimed in claim 7, wherein the bicyclic phosphate compound is 2,6,7-trioxa-phosphobicyclo [2.2.2]-octane-4-methanol-1-oxide; or 2,6,7-trioxa-1-phosphobicyclo[2.2.2]-octane-4-methanol, acetate, 1-oxide.

9. A method, as claimed in claim 7, wherein the weight ratio of bicyclic phosphate compound to flame retardant lies in the range of about 1:25 to 20:1.

10. A method as claimed in claim 7, where the thermoset resin composition additionally comprises glass fiber reinforcements.

11. The composition of claim 1 and which is substantially free of ammonium compounds, amines, ureas, guanidines, guanamines, s-triazines, amino acids and peptides and salts thereof.

12. The composition of claim 10 and which is substantially free of ammonium compounds, amines, ureas, guanidines, guanamines, s-triazines, amino acids, peptides and salts thereof.

* * * * *